(12) United States Patent
Han et al.

(10) Patent No.: US 7,166,737 B2
(45) Date of Patent: Jan. 23, 2007

(54) METHOD FOR MANUFACTURING PHOSPHONATE ESTERS

(75) Inventors: Li-Biao Han, Ibaraki (JP); Farzad Mirzaei, Ibaraki (JP); Masato Tanaka, Ibaraki (JP)

(73) Assignees: Japan Science and Technology Corporation, Saitama (JP); National Institute of Advanced Industrial Science and Technology, Tokyo (JP)

( * ) Notice: Subject to any disclaimer, the term of this patent is extended or adjusted under 35 U.S.C. 154(b) by 52 days.

(21) Appl. No.: 10/853,312

(22) Filed: May 26, 2004

(65) Prior Publication Data

US 2004/0220422 A1 Nov. 4, 2004

Related U.S. Application Data

(62) Division of application No. 09/979,077, filed on Jul. 3, 2002, now Pat. No. 6,765,107.

(30) Foreign Application Priority Data

Mar. 13, 2000 (JP) .............. 2000-069278
Mar. 13, 2000 (JP) .............. 2000-069279

(51) Int. Cl.
*C07F 9/655* (2006.01)
(52) U.S. Cl. ...................................... 558/83
(58) Field of Classification Search .......... 558/83
See application file for complete search history.

(56) References Cited

U.S. PATENT DOCUMENTS 6,949,667 B2 * 9/2005 Han et al. .............. 558/87

FOREIGN PATENT DOCUMENTS

| GB | 2322373 | | 8/1998 |
|----|---------|---|--------|
| JP | 57-48995 | | 3/1982 |
| JP | 2001-247586 | * | 9/2001 |
| JP | 2001-247586 A1 | | 9/2001 |

OTHER PUBLICATIONS

Zhao et al, "Palladium-Catalyzed Hydrophosphorylation of Allenes Leading to Regio- and Stereoselective Formation of Allylphosphonates," Organometallics, vol. 19, p. 4196-4198 (2000).*
European Examination Report (Mar. 28, 2003).
Christen, H. R., "Grundlagen der Oranischen Chemie," pp. 109 & 124, (1982).
Han et al., "High Reactivity of a Five-Membered Cyclic Hydrogen Phosphate," J. Am. Chemical Society, vol. 122, No. 22, pp. 5407-5408 (2000).
Li-Biao Han et al., "Palladium-catalyzed Hydrophosphorylation of Alkynes via Oxidative Addition of HP(O)(OR)2" Journal of the American Chemical Society, 1996, pp. 1571-1572.
Mirzaei et al., "Palladium-catalyzed Hydrophosphorylation of 1,3-dienes Leading to Allyphosphonates", Tetrahedron Letters, 2001, pp. 297-299.
Toshikazu Hirao et al., "Palladium-catalyzed New Carbon-Phosphorus Bond Formation," Bull. Chem. Soc. Jpn., vol. 55, No. 3, pp. 909-913, The Chemical Society of Japan (Mar. 1982).
Xiyan Lu et al., "Nickel Chloride Catalyzed Rearrangement of Allylic Phosphites," J. Organometallic Chemistry, vol. 304, Nos. 1-2, pp. 239-243, Elsevier Sequoia S.A. (1986).
Chang-Qiu Zhao et al., "Palladium-Catalyzed Hydrophosphorylation of Allenes Leading to Regio- and Stereoselective Formation of Allylphosphonates," Organometallic, vol. 19, No. 21, pp. 4196-4198, American Chemical Society (Oct. 2000).
Li-Biao Han et al., "High Reactivity of Five-Membered Cyclic Hydrogen Phosphonate Leading to Development of Facile Palladium-Catalyzed Hydrophosphorylation of Alkenes," 122 J. Am. Chem. Soc.5407-5408 (Jun. 2000).

* cited by examiner

*Primary Examiner*—Joseph K. McKane
*Assistant Examiner*—Andrew B. Freistein
(74) *Attorney, Agent, or Firm*—Rader, Fishman & Grauer PLLC

(57) ABSTRACT

The present invention relates to a new manufacturing method for phosphonate esters, which have utility as a carbon-carbon binding formation agent, as well as a synthesis intermediate for biologically active substances such as medical drugs and agri-chemicals.

Specifically the present invention relates to a new industrially advantageous manufacturing method for phosphonate esters in which the phosphonate esters of the subject can be efficiently obtained with a high yield rate through a simple operation while having barely any side reaction or sub-product.

More specifically, the present invention pertains to a manufacturing method for phosphonate esters in which secondary phosphonate esters and alkene compounds are reacted in a transition metal catalyst. In addition the present invention relates to a new manufacturing method for allylphosphonate esters in which secondary cyclic phosphonate esters and 1,3-diene compounds are reacted in a palladium catalyst.

3 Claims, No Drawings

METHOD FOR MANUFACTURING PHOSPHONATE ESTERS

This application is a Divisional application of Ser. No. 09/979,077, filed Jul. 3, 2002, which issued as U.S. Pat. No. 6,765,107.

TECHNICAL FIELD

The present invention relates to a new manufacturing method for phosphonate esters, which have utility as a carbon-carbon binding formation agent, as well as a synthesis intermediate for biologically active substances such as medical drugs and agri-chemicals.

It has been known that the basic skeleton of the phosphonate esters can be found in nature and by using enzymes, etc., it shows biological activity. For example, through an additive reaction to the carbonyl compounds, the Homer-Emmons reaction is efficiently achieved, and therefore it has been widely used as a synthesizing method for various olefins, and as a synthesizing method for polyenes, which are often found in natural substances for the case of allylphosphonate esters. Therefore, phosphonate esters are effective as carbon-carbon binding formation reagents, and in particular they are compounds that are effective as the synthetic intermediate for medical drugs and agri-chemicals.

BACKGROUND ART

As a method of synthesizing phosphonate esters along with the formation of a carbon-phosphorus bond, in general, the method in which the corresponding halide is substituted with triatkylphosphite has been known. However, with this method, different types of halide compounds are formed along with the reaction and a large volume of by-products are generated. In addition, halides newly generated through the reaction additionally react with the trialkylphophite, so that a disadvantage is that a large volume of sub-products is created. Therefore, the method of the prior art cannot be said to be an industrially advantageous method.

DISCLOSURE OF THE INVENTION

The present invention was created by taking the above-mentioned circumstances into account and its objective is to provide an industrially advantageous manufacturing method for phosphonate esters in which the phosphonate esters of the subject can be obtained with a high yield through a simple operation with a minimum of side reaction or sub-products.

In order to avoid the above-mentioned issues, the present invention was conducted after a diligent study of the reaction of secondary phosphonate esters and alkenes that are easy to obtain, and consequently, it was found that the addition reaction advances in the presence of various transition metal catalysts, and phosphonate esters can be obtained with a high yield, thereby achieving the present invention.

In addition, as a result of a diligent study of the reaction of secondary cyclic phosphonate esters and dienes, which are easy to obtain, it was found that the addition reaction advances in the presence of various palladium catalysts, and the new allylphosphonate esters have a high yield and the present invention was completed.

In other words, the present invention has characteristics such that in the presence of a transition metal catalyst, an alkene compound expressed by the general formula (I):

$$R^1R^2C\!=\!CR^3R^4 \quad\quad (I)$$

(In the formula, each of $R^1$ to $R^4$ individually represents, a hydrogen atom, alkyl group, cycloalkyl group, aryl group or aralkyl group. Also, $R^1$ and $R^4$ can be combined to form an alkylene group.)

is reacted with a secondary phosphonate ester expressed by the general formula (II):

$$HP(O)(OR^5)(OR^6) \quad\quad (II)$$

(In the formula, each of $R^5$ and $R^6$ individually represents an alkyl group, cycloalkyl group, aralkyl group, or aryl group. Also, $R^5$ and $R^6$ can be combined to form an alkylene group with a substitute group.)

It is the invention of a manufacturing method for phosphonate esters expressed as the general formula (III):

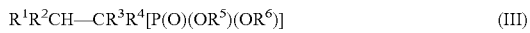
$$R^1R^2CH\!-\!CR^3R^4[P(O)(OR^5)(OR^6)] \quad\quad (III)$$

(In the formula, each of $R^1$ to $R^6$ is the same as above.).

Furthermore, the present invention is characterized such that in the presence of palladium catalyst, a diene compound expressed by the general formula (IV):

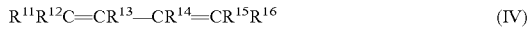
$$R^{11}R^{12}C\!=\!CR^{13}\!-\!CR^{14}\!=\!CR^{15}R^{16} \quad\quad (IV)$$

(In the formula each of $R^{11}$ to $R^{16}$ individually represents a hydrogen atom, alkyl group, cycloalkyl group, aryl group or aralkyl group. Also, $R^{11}$ and $R^{16}$ can be combined to form an alkylene group or cyclo alkylene group.)

is reacted with a secondary cyclic phosphonate ester expressed by the general formula (V):

$$HP(O)X \quad\quad (V)$$

(In the formula, X shows the divalent group of —OC($R^{17}R^{18}$)—C($R^{19}R^{20}$)O—. Here, each of $R^{17}$ to $R^{20}$ shows a hydrogen atom, alkyl group, cycloalkyl group, or aryl group.)

It is the invention of a manufacturing method for allyphosphonate esters expressed by the general formula (VI):

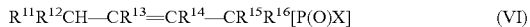
$$R^{11}R^{12}CH\!-\!CR^{13}\!=\!CR^{14}\!-\!CR^{15}R^{16}[P(O)X] \quad\quad (VI)$$

(In the formula, $R^{11}$ to $R^{16}$ and X are the same as above.)

Furthermore, it is an invention for allylphosphonate esters expressed by the general formula (VI):

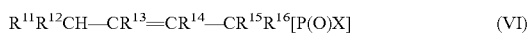
$$R^{11}R^{12}CH\!-\!CR^{13}\!=\!CR^{14}\!-\!CR^{15}R^{16}[P(O)X] \quad\quad (VI)$$

(In the formula, $R^{11}$ to $R^{16}$ and X are the same as above.)

BEST MODE FOR CARRYING OUT THE INVENTION

The examples of the alkyl group expressed as $R^1$ to $R^4$ for the alkene compound expressed in the above-mentioned general formula (I) used for the present invention, and the alkyl group expressed as $R^{11}$ to $R^{16}$ for the diene compound expressed in the above-mentioned general formula (IV) are, alkyl groups with 1 to 18 carbons, and preferably 1 to 10 carbons. These can be either linear or branched and specific examples are, for instance, a methyl group, an ethyl group, a propyl group, a butyl group, a pentyl group, a hexyl group, a heptyl group, an octyl group, a nonyl group, and a decyl group.

In addition, the examples of the cycloalkyl group expressed as $R^1$ to $R^4$ and the cycloalkyl group expressed as $R^{11}$ to $R^{16}$ are, cycloalkyl groups with 5 to 18 carbons, and preferably 5 to 12 carbons. The specific examples are for instance, a cyclopentyl group, a cyclohexyl group, a cycloheptyl group, a cyclooctyl group, a cyclodecyl group and a cyclododecyl group.

Similarly, the examples of an aryl group are an aryl group with 6 to 14 carbons and preferably 6 to 12 carbons, and specific examples are a phenyl group, a tolyl group, an xylyl group, a naphtyl group, a methylnaphtyl group, a penbenzylphenyl group, and a biphenyl group.

Moreover, the examples of an aralkyl group are an aralkyl group with 7 to 13 carbons and preferably 7 to 11 carbons, and specific examples are for instance, a benzyl group, a methylbenzyl group, a phenethyl group, a methylphenethyl group, a phenylbenzyl group and a naphtylmethyl group.

The alkyl group, cycloalklyl group, aryl group and aralkyl group, expressed as the above-mentioned $R^1$ to $R^4$, and the alkyl group, cycloalkyl group, aryl group and aralkyl group expressed as the above-mentioned $R^{11}$ to $R^{16}$ can be substituted with inert functional groups for the reaction, for example, alkyl groups such as a methyl group or an ethyl group, alkoxy groups such as a methoxy group or an ethoxy group, alkoxycarbonyl groups such as a methoxy carbonyl group or an ethoxy carbonyl group, a cyano group, an N,N-di-substituted amino group such as a dimethylamino group or diethylamino group, and a fluoro group.

The examples of an alkylene group in the general formula (I) in which $R^1$ and $R^4$ are combined to form an alkylene group, and the alkylene group in the general formula (IV), in which $R^{11}$ and $R^{16}$ are combined to form an alkylene group are an alkylene group with 1 to 20 carbons, and more preferably 1 to 10 carbons. Specific examples are, for instance, a methylene group, an ethylene group, a trimethylene group, and a tetramethylene group.

The examples of the cycloalkylene group in the general formula (IV) in which $R^{11}$ and $R^{16}$ are combined to form a cycloalkylene group are, cycloalkylene group with 5 to 18 carbons, and more preferably 5 to 10 carbons, and specific examples are, for instance, a cyclopentylene group, a cyclohexylene group, a cycloheptylene group, a cyclooctylene group, a cyclononylene group, and a cyclodecylene group.

The examples of an alkene compound preferably used in the present invention are, ethylene, propylene, octene, styrene, norbornene, cyclopentene, and cyclohexene, however it is not limited to these.

The examples of a diene compound preferably used in the present invention are, for instance, 1,3-butadiene, isoprene, 1,3-pentadiene, and 2,3-dimethyl-1,3-butadiene, however, it is not limited to these.

In the general formula (IV), when the alkylene group or the cycloalkylene group are a combination of $R^{11}$ and $R^{16}$, said diene compound is a cyclic diene compound. Specific examples of the cyclic diene compounds are, for instance, 1,3-cyclopentadiene, and 1,3-cyclohexadiene, however, it is not limited to these.

In the present invention, the examples of alkyl groups expressed as $R^5$ and $R^6$ in the secondary phosphonate esters expressed by the above-mentioned general formula (II), and the alkyl groups expressed as $R^7$ to $R^{10}$ of the divalent groups, which is $-OC(R^{17}R^{18})-C(R^{19}R^{20})O-$ which is indicated as the X of the secondary cyclic phosphonate esters expressed by the above-mentioned general formula (V), are alkyl groups with 1 to 8 carbons, and more preferably 1 to 6 carbons. These can be either linear or branched types, and specific examples are, for instance, a methyl group, an ethyl group, a propyl group, a butyl group, a pentyl group, and a hexyl group.

In addition, examples of said cycloalkyl group are, a cycloalkyl group with 3 to 12 carbons, and more preferably 5 to 8 carbons, and specific examples are, for instance, a cyclopentyl group, a cyclohexyl group, a cycloheptyl group, and a cyclooctyl group.

Similarly, examples of said aryl group are, an aryl group with 6 to 14 carbons, and more preferably 6 to 12 carbons, and specific examples are, for instance, a phenyl group, a tolyl group, a xylyl group, a naphtyl group, a methylnaphtyl group, a benzylphenyl group, and a biphenyl group.

Moreover, the examples of an aralkyl group expressed as $R^5$ and $R^6$ in the general formula (II) are aralkyl groups with 7 to 13 carbons, and more preferably 7 to 11 carbons, and specific examples are, for instance, a benzyl group, a methyl benzyl group, a phenetyl group, a methylphenetyl group, a phenylbenzyl group and a naphtylmethyl group.

The examples of an alkylene group in the case $R^5$ and $R^6$ in the general formula (II) are combined and form an alkylene group with a substitute group, are, for instance, a methylene group, an ethylene group, a trimethylene group and a tetramethylene group. In addition, examples of substitute groups for these alkylene groups are, for instance, an alkyl group, a cyclo alkyl group, an aralkyl group and an aryl group.

Here, examples of an alkyl group are alkyl groups with 1 to 8 carbons and more preferably 1 to 6 carbons. These can be either linear or branched types, and specific examples are, for instance, a methyl group, an ethyl group, a propyl group, a butyl group, a pentyl group and a hexyl group.

Furthermore, examples of cylcoalkyl groups are cycloclkyl groups with 3 to 12 carbons, and more preferably 5 to 8 carbons, and specific examples are, for instance, a cyclopentyl group, a cyclohexyl group, a cyclohebutyl group, and a cyclooctyl group.

Examples of aralkyl groups are aralkyl groups with 7 to 13 carbons, and more preferably 7 to 11 carbons and specific examples are, for instance, a benzyl group, a methyl benzyl group, a phenetyl group, a methyl phenetyl group, a phenylbenzyl group, and a naphtylmethyl group.

The examples of aryl groups are aryl groups with 6 to 14 carbons, and more preferably 6 to 12 carbons, and specific examples are, for instance, a phenyl group, a tolyl group, a xylyl group, a naphtyl group, a methyl naphtyl group, a benzylphenyl group, and a biphenyl group.

In order to efficiently promote the reaction of the alkene compound expressed by the general formula (I) and the secondary phosphonate esters expressed by the general formula (II), the use of a transition metal catalyst is essential. When there is no catalyst, the reaction does not advance or is extremely slow. A catalyst with a variety of structures can be used, but those with a low valence are preferable, and transition metal catalysts that are carried by carriers such as an active carbon or silica, or a transition metal complex in which a variety of ligands are coordinated can be used. In particular, nickel, palladium catalyst and rhodium are the preferable transition metals. A zerovalent complex with a ligand of a tertiary phosphine or a tertiary phosphine is even more preferable as the nickel or palladium catalyst, and a monovalent complex is even more preferable as the rhodium complex. In addition, it is a desirable means to use an appropriate precursor complex that can be easily converted to a low valence complex in the reaction system. Moreover, it is a desirable means to have a complex that does not contain a tertiary phosphine or tertiary phosphine as a ligand, and where a tertiary phosphine and phosphite are used together, and a low valence complex with a ligand of a tertiary phosphine or phosphite is formed in the reaction system. In either of the above-mentioned methods, examples of the ligand that has the most advantageous properties are, a variety of tertiary phosphines and tertiary phosphites. However, those with extremely strong electron donor levels are not necessarily advantageous in terms of reaction speed. Examples of desirable ligands are, triphenylphophine, diphenylmethylphosphine, phenyldimethylphosphine, 1,4-bis (diphenylphosphino) butane, 1,3-bis (diphenylphosphino) propane, 1,2-bis (diphenylphosphino) ethane, 1,1'-bis (diphenylphosphino) ferrocene, trimethylphosphite, and triphenylphosphite. Examples of a complex that do not have a tertiary phosphine or tertiary phospite as a ligand, which are used in combination with the above are, a bis (1,5-cyclooctadiene) nickel complex, a bis (dibenzylideneacetone) palladium complex, palladium acetate complex, a chloro (1,5-cyclooctadiene) rhodium complex, and a chloro (norbornaediene) rhodium complex, however it is not limited to the above. Examples of a phosphine complex and a phosphite complex that are preferably used are, a tetrakis (triphenylphosphine) nickel complex, a dimethylbis (triphenylphosphine) palladium complex, a dimethylbis (diphenylmethylphophine) palladium complex, tetrakis (triphenylphosphine) palladium complex and a chlorotris (triphenylphosphine) rhodium complex.

One of two or more appropriate transition metal catalysts, depending on the reaction are used.

The amount of these transition metal catalysts can acceptably be called a catalyst amount, and in general, it is sufficient to be 20 mol % or less per alkene compound. The usage ratio of the alkene compound and the secondary phosphonate esters is, in general, desired to be a 1:1 mole ratio, however, being greater or less than this value does not hinder the promotion of the reaction. A solvent does not need to be used during the reaction, however, it is possible to be carried out in a solvent as required. Examples of solvents that are generally used are, for instance, a hydrocarbon solvent such as benzene, toluene, xylene, n-hexane, cyclohexane, or for instance, an ether solvent such as dimethylether, diethylether, diisopropylether, 1,4-dioxane, and tetrahydrofuran. When the reaction temperature is too low, the reaction does not advance at an advantageous speed and when it is too high, the catayst is decomposed. Therefore, in general, it is selected from the range of room temperature to 300° C., and more preferably, it is carried out in the range from 50 to 150° C.

The intermediate of the present reaction is sensitive to oxygen, therefore, it is desirable to carry out the reaction in an inert gas atmosphere such as nitrogen, argon, or methane. The isolation and purification of the product from the reaction compound can be easily achieved with well-known isolation and purification methods that have been normally conducted in this field such as chromatography, distillation or recrystallization.

In addition, in order to efficiently promote the reaction of the diene compound expressed by the general formula (IV) and the secondary cyclic phosphonate esters expressed by the general formula (V), the use of a palladium catalyst is essential. When there is no catalyst, the reaction does not advance or is extremely slow. A catalyst with a variety of structures can be used, but those with a low valence are preferable, and a zerovalent complex with a ligand of a tertiary phosphine or a tertiary phosphine is preferable. In addition, it is a desirable means to use an appropriate precursor complex that can be easily converted to a low valence complex in the reaction system. Moreover, it is a desirable means to form a low valence complex with a ligand of a tertiary phosphine or tertiary phosphite in the reaction system by using a complex that does not contain a tertiary phosphine or tertiary phosphite as a ligand, and a tertiary phosphine and tertiary phosphite together. In either of the above-mentioned methods, examples of the ligand that has the most advantageous properties are a variety of tertiary phosphines and tertiary phosphites. However, those with extremely strong electron donor levels are not necessarily advantageous in terms of reaction speed. Examples of desirable ligands are, triphenylphophine, diphenylmethylphosphine, phenyldimethylphosphine, 1,4-bis (diphenylphosphino) butane, 1,3-bis (diphenylphosphino) propane, 1,2-bis (diphenylphosphino) ethane, 1,1'-bis (diphenylphosphino) ferrocene, trimethylphosphite, and triphenylphosphite. Examples of a complex that does not have a tertiary phosphine or tertiary phospite as a ligand, which is used in combination with the above are, a bis (dibenzylideneacetone) palladium complex and a palladium acetate complex, however it is not limited to the above. Examples of a phosphine complex and a phosphite complex that are preferably used are, a dimethylbis (triphenylphosphine) palladium complex, a dimethylbis (diphenylmethylphophine) palladium complex, and tetrakis (triphenylphosphine) palladium complex.

One of two or more appropriate palladium complex catalysts of the present invention, depending on the reaction are used.

The amount of these complex catalysts can acceptably be called a catalyst amount, and in general, it is sufficient to be 20 mol % or less per diene compound. The usage ratio of the diene compound and the secondary cyclic phosphonate esters is, in general, desired to be a 1:1 mole ratio, however, being greater or less than this value does not hinder the promotion of the reaction. A solvent does not need to be used during the reaction, however, it is possible to be carried out in a solvent as required. Examples of solvents that are generally used are, for instance, a hydrocarbon solvent such as benzene, toluene, xylene, n-hexane, cyclohexane, or for instance, an ether solvent such as dimethylether, diethylether, diisopropylether, 1,4-dioxane, and tetrahydrofuran. When the reaction temperature is too low, the reaction does not advance at an advantageous speed and when it is too high, the catalyst is decomposed. Therefore, in general, it is selected from the range of room temperature to 300° C., and more preferably, it is carried out in the range from 50 to 150° C.

The intermediate of the present reaction is sensitive to oxygen, therefore, it is desirable to carry out the reaction in an inert gas atmosphere such as nitrogen, argon, or methane. The isolation and purification of the product from the reaction compound can be easily achieved with well-known isolation and purification methods that have been normally conducted in this field such as chromatography, distillation or recrystallization.

The present invention is further described in detail using the following examples, however, the present invention is not limited by these examples.

EXAMPLES

Example 1

A 1 mmol of $HP(O)(OCMe_2-Me_2CO)$, 1 mmol of 1-octene, and $PdMe_2(PPh_2Me)_2$ (5 mol %) as a catalyst were added to 1 ml of toluene, and the reaction was carried out in a nitrogen atmosphere at 110° C. for 3 hours. The reacted liquid was condensed and isolated and purified using liquid chromatography, and then 2-octyl-4,4,5,5-tetramethyl-1,3,2-dioxaphosphorane 2-oxide was obtained with a 63% yield.

This compound is a new substance that is not mentioned in any documents and its spectrum data is as follows.

$^1$H NMR (500 MHz, $CDCl_3$) δ 1.79–1.86 (dt, 2H, J=7.3 Hz, $J_{HP}$=17.1 Hz), 1.64–1.74 (m, 2H), 1.47 (s, 6H), 1.34–1.43 (m, 2H), 1.33 (s, 6H), 1.18–1.31 (m, 8H), 0.86 (t, 3H, J=7.0 Hz). $^{13}$C NMR (125.4 MHz, $CDCl_3$) δ 87.7, 31.8, 30.7 ($J_{CP}$=16.5 Hz), 29.1 ($J_{CP}$=3.1 Hz), 28.2 ($J_{CP}$=130.9 Hz), 24.8 ($J_{CP}$=4.1 Hz), 24.1 (d, $J_{CP}$=5.2 Hz), 22.9, 22.8, 22.6, 14.1. $^{31}$P NMR (201.9 MHz, $CDCl_3$) δ 44.4. IR (liquid membrane) 2927, 2856, 1463, 1396, 1377, 1261, 1140, 1010, 964, 931, 872, 802, 731 $cm^{-1}$. HRMS as $C_{14}H_{29}O_3P$, Calculated value: 276.1854, Actual value: 276.1860.

Example 2

Under similar conditions to Example 1, using $Pd(PPh_3)_4$ as a catalyst, a reaction was carried out. 2-octyl-4,4,5,5-tetramethyl-1,3,2-dioxaphosphorane2-oxide was obtained with a 46% yield.

Example 3

Under similar conditions to Example 1, using $PdMe_2[Ph_2P(CH_2)_3PPh_2]$ as a catalyst, a reaction was carried out. 2-octyl-4,4,5,5-tetramethyl-1,3,2-dioxaphosphorane2-oxide was obtained with a 22% yield.

Example 4

Under similar conditions to Example 1, using $PdMe_2[Ph_2P(CH_2)_4PPh_2]$ as a catalyst, a reaction was carried out. 2-octyl-4,4,5,5-tetramethyl-1,3,2-dioxaphosphorane2-oxide was obtained with a 45% yield.

Example 5

Under similar conditions to Example 1, using $Ni(PPh_3)_4$ as a catalyst, a reaction was carried out. 2-octyl-4,4,5,5-tetramethyl-1,3,2-dioxaphosphorane2-oxide was obtained with a 26% yield.

Example 6

Under similar conditions to Example 1, using $RhCl(PPh_3)_3$ as a catalyst, a reaction was carried out. 2-octyl-4,4,5,5-tetramethyl-1,3,2-dioxaphosphorane2-oxide was obtained with a 49% yield.

Example 7

A 1 mmol of $HP(O)(OCMe_2-Me_2CO)$, 1 mmol of 1-octene, and $PdMe_2[Ph_2P(CH_2)_4PPh_2]$ (5 mol %) as a catalyst were added to 1 ml of 1,4-dioxane, and the reaction was carried out in a nitrogen atmosphere at 100° C. for 15 hours. The reacted liquid was condensed and isolated and purified using liquid chromatography, and then 2-octyl-4,4,5,5-tetramethyl-1,3,2-dioxaphosphorane 2-oxide was obtained with a 93% yield.

Example 8

Under similar conditions to Example 7, using $PdMe_2[Ph_2P(CH_2)_3PPh_2]$ as a catalyst, a reaction was carried out. 2-octyl-4,4,5,5-tetramethyl-1,3,2-dioxaphosphorane2-oxide was obtained with a 33% yield.

Example 9

Under similar conditions to Example 7, using $PdMe_2(PPh_2Me)_2$ as a catalyst, a reaction was carried out. 2-octyl-4,4,5,5-tetramethyl-1,3,2-dioxaphosphorane2-oxide was obtained with a 54% yield.

Example 10

A 1 mmol of $HP(O)(OCMe_2-Me_2CO)$, 1 mmol of 1-octene, and a composition of $Pd_2(dba)_3/Ph_2P(CH_2)_4PPh_2$ (5 mol Pd %, Pd/P mole ratio=1/2) as a catalyst were added to 1 ml of 1,4-dioxane, and the reaction was carried out in a nitrogen atmosphere at 100° C. for 15 hours. The reacted liquid was condensed and isolated and purified using liquid chromatography, and then 2-octyl-4,4,5,5-tetramethyl-1,3,2-dioxaphosphorane 2-oxide was obtained with an 82% yield.

Example 11

A 1 mmol of $HP(O)(OMe)_2$ and a composition of $PdMe_2[Ph_2P(CH_2)_4PPh_2]$ (5 mol %) as a catalyst were added to 1 ml of 1,4-dioxane, and the reaction was carried out in a ethylene atmosphere (5 atm) at 100° C. for 15 hours. The reacted liquid was condensed and isolated and purified using liquid chromatography, and then dimethyl ethylphosphonate [$EtP(O)(OMe)_2$] was obtained with a 63% yield. This compound is a known compound and the structure was determined by comparing it with a standard sample.

Example 12

Instead of $HP(O)(OMe)_2$, $HP(O)(OCMe_2-Me_2CO)$ was used and by carrying out a reaction in a similar manner to Example 11, 2-ethyl-4,4,5,5-tetramethyl-1,3,2-dioxaphosphorane2-oxide was quantitatively obtained. This compound is a known compound and its spectrum data is as follows.

$^1$H NMR (300 MHz, $CDCl_3$) δ 1.68 (dq, 2H, $J_{HP}$=17.6 Hz, $J_{HH}$=7.7 Hz), 1.32 (s, 6H), 1.18 (s, 6H), 1.09 (dt, 3H, $J_{HP}$=20.2 Hz, J=7.7 Hz). $^{13}$C NMR (75.5 MHz, $CDCl_3$) δ 87.7 ($J_{CP}$=1.5 Hz), 24.6 ($J_{CP}$=3.7 Hz), 23.9 ($J_{cp}$=5.3 Hz), 21.0 ($J_{CP}$=134.2 Hz), 6.9 ($J_{CP}$=6.7 Hz). $^{31}$P NMR (121.5 MHz, $CDCl_3$) δ 45.3. IR (liquid membrane) 2988, 2946, 1462, 1398, 1379, 1265, 1232, 1168, 1141, 1011, 963, 932, 870, 806, 729 $cm^{-1}$. HRMS as $C_8H_{17}O_3P$, Calculated value: 192.0915, Actual value: 192.0890.

Example 13

Instead of ethylene gas, propylene gas was used and by reacting it in a similar manner to that of Example 12, 2-propyl-4,4,5,5-tetramethyl-1,3,2-dioxaphosphorane2-oxide was quantitatively obtained. The spectrum data of this compound is as follows.

$^1$H NMR (300 MHz, $CDCl_3$) δ 1.64–1.80 (m, 4H), 1.42 (s, 6H), 1.28 (s, 6H), 0.98 (t, 3H, J=7.3 Hz). $^{13}$C NMR (75.5

MHz, CDCl$_3$) δ 87.7 (J$_{CP}$=1.5 Hz), 30.1 (J$_{CP}$=131.5 Hz), 24.7 (J$_{cp}$=3.8 Hz), 24.0 (J$_{CP}$=5.3 Hz), 16.6 (J$_{CP}$=5.3 Hz), 15.3 (J$_{CP}$=16.0 Hz). $^{31}$P NMR (121.5 MHz, CDCl$_3$) δ 44.1. IR (liquid membrane)2972, 2880, 1464, 1398, 1379, 1263, 1214, 1170, 1141, 1011, 965, 934, 872, 803, 714 cm$^{-1}$. HRMS as C$_9$H$_{19}$O$_3$P, Calculated value: 206.1072, Actual value: 206.1053.

Example 14

Instead of ethylene gas, 3,3-dimethyl-1-buten was used and by reacting it in a similar manner to that of Example 12, 2-(3,3-dimethylbutyl)-4,4,5,5-tetramethyl-1,3,2-dioxaphosphorane2-oxide was quantitatively obtained with a 92% yield. The spectrum data and the elemental analysis of this compound are as follows.

$^1$H NMR (500 MHz, CDCl$_3$) δ 1.72–1.80 (m, 2H), 1.55–1.61 (m, 2H), 1.46 (s, 6H), 1.32 (s, 6H), 0.86 (s, 9H). $^{13}$C NMR (125.4 MHz, CDCl$_3$) δ 87.8, 36.2 (J$_{CP}$=5.3 Hz), 30.4 (J$_{CP}$=17.6 Hz), 28.7, 24.8 (J$_{CP}$=10.3 Hz), 24.1 (J$_{CP}$=5.1 Hz), 23.6 (J$_{CP}$=133.3 Hz) $^{31}$P NMR (201.9 MHz, CDCl$_3$) δ 45.4. IR (KBr)2934, 2868, 1469, 1396, 1377, 1367, 1261, 1169, 1140, 1014, 964, 933, 874, 835, 806 cm$^{-1}$. HRMS as C$_{12}$H$_{25}$O$_3$P, Calculated value: 248.1541. Actual value: 248.1544. Elemental analysis, Calculated value: C, 58.05; H, 10.15. Actual value: C, 58.47; H, 10.14.

Example 15

Instead of ethylene gas, norbornene was used and by reacting it in a similar manner to that of Example 12, 2-exo-norbornyl-4,5,5,5-tetramethyl-1,3,2-dioxaphosphorane 2-oxide was obtained with a 83% yield. The spectrum data and the elemental analysis of this compound are as follows.

$^1$H NMR (500 MHz, CDCl$_3$) δ 2.64 (d, 1H, J$_{HP}$=8.8 Hz), 2.32 (bs, 1H), 1.87–1.98 (m, 1H), 1.75 (d, 1H, J=9.8 Hz), 1.46–1.57 (m, 4H), 1.49 (s, 3H), 1.47 (s, 3H), 1.34 (s, 3H), 1.33 (s, 3H), 1.08–1.22 (m, 3H). $^{13}$C NMR (125.4 MHz, CDCl$_3$) δ 87.6 (J$_{CP}$=9.3 Hz), 40.3 (J$_{CP}$=133.3 Hz), 38.8 (J$_{CP}$=2.1 Hz), 37.0, 36.0(J$_{CP}$=3.1 Hz), 32.4 (J$_{CP}$=6.3 Hz), 31.6(J$_{CP}$=18.7 Hz), 28.6, 24.9 (J$_{CP}$=3.0 Hz), 24.8 (J$_{CP}$=4.1 Hz), 24.3 (J$_{CP}$=6.3 Hz), 24.2 (J$_{CP}$=5.1 Hz). $^{31}$P NMR (201.9 MHz, CDCl$_3$) δ 45.6. IR (KBr) 2956, 2871, 1396, 1377, 1257, 1167, 1140, 1012,960,868,800,615 cm$^{-1}$. HRMS as C$_{13}$H$_{23}$O$_3$P, Calculated value: 258.1385, Actual value: 258.1369. Elemental analysis, Calculated value: C, 60.45; H, 8.98. Actual value: C, 60.64; H, 9.02.

Example 16

Instead of ethylene gas, cyclopentene was used and by reacting it in a similar manner to that of Example 12, 2-cyclopentyl-4,4,5,5-tetramethyl-1,3,2-dioxaphosphorane 2-oxide was obtained with a 54% yield. The spectrum data and the elemental analysis of this compound are as follows.

$^1$H NMR (500 MHz, CDCl$_3$) δ 1.57–1.88 (m, 9H), 1.43 (s, 6H), 1.29 (s, 6H). $^{13}$C NMR (125.4 MHz, CDCl$_3$) δ 87.6, 37.4 (J$_{CP}$=136.4 Hz), 27.9 (J$_{CP}$=3.0 Hz), 26.2 (J$_{CP}$=12.4 Hz), 24.8 (J$_{CP}$=4.1 Hz), 24.2 (J$_{CP}$=6.1 Hz). $^{31}$P NMR (201.9 MHz, CDCl$_3$) δ 48.0. IR (KBr) 3001, 2985, 2964, 2873, 1392, 1377, 1259, 1169, 1147, 1130, 960, 926, 870, 800 cm$^{-1}$. HRMS as C$_{11}$H$_{21}$O$_3$P, Calculated value: 232.1228, Actual value: 232.1253.

Example 17

Instead of ethylene gas, cyclohexene was used and by reacting it in a similar manner to that of Example 12, 2-cyclohexyl-4,4,5,5-tetramethyl-1,3,2-dioxaphosphorane 2-oxide was obtained with a 37% yield. The spectrum data and the elemental analysis of this compound are as follows.

$^1$H NMR (500 MHz, CDCl$_3$) δ 1.95–2.03 (m, 2H), 1.75–1.84 (m, 2H), 1.62–1.72 (m, 2H), 1.47 (s, 6H), 1.32 (s, 6H), 1.17–1.57 (m, 5H). $^{13}$C NMR (125.4 MHz, CDCl$_3$) δ 87.5 (J$_{CP}$=2.0 Hz), 38.1 (J$_{CP}$=133.3 Hz), 26.2 (J$_{CP}$=4.1 Hz), 26.0 (J$_{CP}$=16.4 Hz), 25.7, 25.0 (J$_{CP}$=4.1 Hz), 24.4 (J$_{CP}$=5.1 Hz). $^{31}$P NMR (201.9 MHz, CDCl$_3$) δ 45.2. IR (KBr) 2987, 2941, 2883, 2844, 1452, 1396, 1377, 1255, 1170, 1145, 1120, 960, 922, 860, 800 cm$^{-1}$. HRMS as C$_{12}$H$_{23}$O$_3$P, Calculated value: 246.1385. Actual value: 246.1365. Elemental analysis, Calculated value: C. 58.52; H, 9.41. Actual value: 58.86; H, 9.57

Example 18

Instead of ethylene gas, styrene was used and by reacting it in a similar manner to that of Example 12, 2-(1-phenylethyl)-4,4,5,5-tetramethyl-1,3,2-dioxaphosphorane 2-oxide was obtained with a 45% yield, and 2-(2-phenylethyl)-4,4,5,5-tetramethyl-1,3,2-dioxaphosphorane 2-oxide was obtained with a 55% yield. The spectrum data and the elemental analysis of this compound are as follows. Regarding 12 2-(1-phenylethyl)-4,4,5,5-tetramethyl-1,3,2-dioxaphosphorane 2-oxide:

$^1$HNMR (500 MHz, CDCl$_3$) δ 7.18–7.41 (m, 5H), 3.18 (dq, 1H, J$_{HH}$=7.3, J$_{HP}$=21.0 Hz), 1.68 (dd, 3H, J=7.3, J$_{HP}$=18.6 Hz), 1.46 (s, 3H), 1.42 (s, 3H), 1.17 (s, 3H), 1.13 (s, 3H). $^{13}$C NMR (125.4 MHz, CDCl$_3$) δ 137.8 (J$_{CP}$=7.2 Hz), 128.7 (J$_{CP}$=6.2 Hz), 128.6, 127.3 (J$_{CP}$=3.1 Hz), 88.1 (J$_{CP}$=10.3 Hz), 40.2 (J$_{CP}$=128.3 Hz), 25.1, 25.0, 24.1, 23.9, 16.3 (J$_{CP}$=5.2 Hz). $^{31}$P NMR (201.9 MHz, CDCl$_3$) δ 41.9. IR (KBr) 2985, 2939, 1454, 1396, 1377, 1263, 1232, 1169, 1132, 1008, 964, 935, 876, 800, 771, 702 cm$^{-1}$. HRMS as C$_{14}$H$_{21}$O$_3$P, Calculated value: 268.1228. Actual value: 268.1205. Elemental analysis, Calculated value: C, 62.67; H, 7.89. Actual value: C, 62.46; H, 7.98.

Regarding 2-(2-phenylethyl)-4,4,5,5-tetramethyl-1,3,2-dioxaphosphorane 2-oxide:

$^1$H NMR (500 MHz, CDCl$_3$) δ 7.20–7.38 (m, 5H), 2.98–3.05 (m, 2H), 2.12–2.19 (m, 2H), 1.50 (s, 6H), 1.34 (s, 6H). $^{13}$C NMR (125.4 MHz, CDCl$_3$) δ 141.0 (J$_{CP}$=17.6 Hz), 128.6, 128.1, 126.4, 88.1 (J=13.4 Hz), 30.2 (J$_{CP}$=130.3 Hz), 29.0 (J$_{CP}$=4.1 Hz), 24.8 (J$_{CP}$=3.1 Hz), 24.1 (J$_{CP}$=5.1 Hz). $^{31}$P NMR (201.9 MHz, CDCl$_3$) δ 42.5.

Example 19

Instead of PdMe$_2$[Ph$_2$P(CH$_2$)$_4$PPh$_2$], PdMe$_2$(PPh$_2$Cy)$_2$ was used and by reacting it in a similar manner to that of Example 182-(1-phenylethyl)-4,4,5,5-tetramethyl-1,3,2-dioxaphosphorane 2-oxide was obtained with a 97% yield.

Example 20

A 2 mmol of HP(O)(OCMe$_2$—CMe$_2$O), 2 mmol of 2,3-dimethyl-1,3-butadiene, and PdMe$_2$[Ph$_2$P(CH$_2$)$_4$PPh$_2$] (5 mol %) as a catalyst were added to 3 ml of 1,4-dioxane, and the reaction was carried out in a nitrogen atmosphere at 100° C. for 12 hours. The reacted liquid was condensed and isolated and purified using liquid chromatography, and then 2-(2,3-dimethyl-2-butenyl)-4,4,5,5-tetramethyl-1,3,2-dioxaphosphorane 2-oxide [Me$_2$C=CMeCH$_2$P(O){OCMe$_2$CMe$_2$O}] was obtained with a 100% yield.

This compound is a new substance that is not mentioned in any documents and its spectrum data is as follows.

$^1$H NMR(500 MHz, CDCl$_3$) δ 2.64 (d, 2H, J$_{HP}$=21.7 Hz), 1.56–1.67 (m, 12H), 1.37 (s, 6H), 1.21 (s, 6H). $^{13}$C NMR (125.4 MHz, CDCl$_3$) δ 129, 117.8, 87.6, 33.5 (J$_{CP}$=128.0 Hz), 24.8, 23.9, 21.0, 20.7, 20.0. $^{31}$P NMR (201.9 MHz, CDCl$_3$) δ 40.4. IR (liquid membrane) 2988, 2922, 1450, 1398, 1379, 1265, 1139, 963, 932, 872 cm$^{-1}$. HRMS as C$_{12}$H$_{23}$O$_3$P, Calculated value: 246.1385. Actual value: 246.1398.

Example 21

Instead of 2,3-dimethyl-1,3-butadiene, 1,3-butadiene was used in the presence of PdMe$_2$(binap)(binap=2,2'-bis(diphenylphosphino)-1,1'-binaphthyl) catalyst, and by reacting them in a similar manner to that of Example 20, the compounds shown in Table 1 were obtained with the total yield rate of 100% (trans form/cis form=83/17). These compounds are new substances that are not mentioned in any documents and their spectrum data is as follows.

Trans Form Compound $^1$H NMR (500 MHz, CDCl$_3$) δ 5.57–5.62 (m, 1H), 5.39–5.45 (m, 1H), 2.62 (dd, 2H, J=7.3, J$_{HP}$=21.3 Hz), 1.64–1.68 (m, 3H), 1.45 (s, 6H), 1.30 (s, 6H). $^{13}$C NMR (125.4 MHz, CDCl$_3$) δ 130.9 (J$_{CP}$=14.51 Hz), 119.5 (J$_{CP}$=12.4 Hz), 88.0, 32.0 (J$_{CP}$=131.4 Hz), 24.7, 24.4, 18.0. $^{31}$P NMR (201.9 MHz, CDCl$_3$) δ 39.5.

Cis Form Compound $^1$H NMR (500 MHz, CDCl$_3$) δ 5.65–5.72 (m, 1H), 5.40–5.50 (m, 1H), 2.70 (dd, 2H, J=7.9, J$_{HP}$=21.9 Hz), 1.61–1.64 (m, 3H), 1.45 (s, 6H), 1.32 (s, 6H). $^{13}$C NMR (125.4 MHz, CDCl$_3$) δ 129.0 (J$_{CP}$=14.5 Hz), 118.5 (J$_{CP}$=11.4 Hz), 88.0, 27.0 (J$_{CP}$=132.4 Hz), 24.7, 23.8, 12.9. $^{31}$P NMR (201.9 MHz, CDCl$_3$) δ 39.6.

Example 22

Instead of 2,3-dimethyl-1,3-butadiene, isoprane was used and by reacting it in a similar manner to that of Example 20 the compounds shown in Table 1 were obtained with the total yield rate of 100% (products rate=83/17). These compounds are new substances that are not mentioned in any documents and their spectrum data is as follows.

$^1$H NMR (500 MHz, CDCl$_3$) δ 5.18–5.23 (m, 1H), 2.68 (dd, 2H, J=7.6 Hz, J$_{HP}$=21.3 Hz), 1.74 (d, 3H, J$_{HP}$=5.8 Hz), 1.65 (d, 3H, J$_{HP}$=4.0 Hz), 1.48 (s, 6H), 1.34 (s, 6H). $^{13}$C NMR (125.4 MHz, CDCl$_3$) δ 137.0, 112.6, 87.8,28.0 (J$_{CP}$=131.2 Hz), 25.7, 24.2, 18.0. $^{31}$P NMR (201.9 MHz, CDCl$_3$) δ 40.3.

Example 23

Instead of 2,3-dimethyl-1,3-butadiene, trans-1,3-pantadiene was used in the presence of a PdMe$_2$(dppf)(dppf=1,1'-bis(diphenylphosphino) ferrocene) catalyst, and by reacting them in a similar manner to that of Example 20, the compounds shown in Table 1 were obtained with the total yield rate of 93% (trans form/cis form=92/8). These compounds are new substances that are not mentioned in any documents and their spectrum data is as follows.

$^1$H NMR (500 MHz, CDCl$_3$) δ 5.25–5.36 (m, 1H), 5.08–5.12 (m, 1H), 2.33 (dd, 2H, J=7.4 Hz, J$_{HP}$=21.1 Hz), 1.70–1.78 (m, 2H), 1.17 (s, 6H), 1.03 (s, 6H), 0.66 (t, 3H, J=7.6 Hz). $^{13}$C NMR (125.4 MHz, CDCl$_3$) δ 137.7, 117.5, 88.0, 32.0 (J$_{CP}$=132.3 Hz), 25.6, 24.9, 24.2, 13.3. $^{31}$P NMR (201.9 MHz, CDCl$_3$) δ 39.0. IR (film) 2988, 1462, 1398, 1379, 1267, 1139, 1011, 963, 932, 874 cm$^{-1}$.

Example 24

Instead of 2,3-dimethyl-1,3-butadiene, cyclo-1,3-hexadiene was used in the presence of a PdMe$_2$[Ph$_2$P(CH$_2$)$_4$PPh$_2$] catalyst, and by reacting them in a similar manner to that of Example 20, the compounds shown in Table 1 were obtained with the total yield rate of 100%. These compounds are new substances that are not mentioned in any documents, and their spectrum data and the elemental analysis of this compound are as follows.

$^1$H NMR (500 MHz, CDCl$_3$) δ 5.83–5.90 (m, 1H), 5.63–5.72 (m, 1H), 2.59–2.64 (m, 1H), 1.94–2.00 (m, 6H), 1.48 (s, 3H), 1.46 (s, 3H), 1.32 (s, 6H). $^{13}$C NMR (125.4 MHz, CDCl$_3$) δ 131.3, 121.1,87.8,36.5 (J$_{CP}$=132.2 Hz), 25.1, 24.9, 24.5, 24.4, 22.8, 20.5. $^{31}$P NMR (201.9 MHz, CDCl$_3$) δ 42.6. IR (KBr) 2989, 2869, 1454, 1392, 1376, 1263, 1145, 1132, 958, 923, 867 cm$^{-1}$. HRMS as C$_{12}$H$_{21}$O$_3$P, Calculated value: 244.1228. Actual value: 244.1252. Elemental analysis, Calculated value: C, 59.00; H, 8.67. Actual value: C, 59.12; H, 8.00.

Table 1 shows structural formulas and yields of products obtained from above examples 20 to 24 together with structural formulas of each starting material.

TABLE 1

| Example | Diene | Adducts* | Yield % |
|---|---|---|---|
| 20 | | | 100 |
| 21 | | (Trans form/cis form: 83/17) | 100 |
| 22 | | (Product ratio: 83/17) | 100 |
| 23 | | (Trans form/cis form: 92/8) | 93 |
| 24 | | | 100 |

*X$_2$ = OCMe$_2$—Me$_2$CO 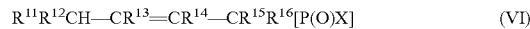

INDUSTRIAL APPLICABILITY

The present invention is effective as a carbon-carbon binding formation reagent, and in addition, it allows the simple, safe and efficient synthesis of phosphonate esters (including new allylphosphonate esters) that are useful to synthesize medical drugs and agri-chemicals. Its isolation and purification is simple as well. Therefore the present invention has a significant industrial effect.

The invention claimed is:

1. An allylphosphonate ester expressed by general formula (VI):

R$^{11}$R$^{12}$CH—CR$^{13}$=CR$^{14}$—CR$^{15}$R$^{16}$[P(O)X]    (VI)

wherein each of R$^{11}$ through R$^{16}$ individually represents a hydrogen atom, alkyl group, cycloalkyl group, aryl group or aralkyl group, wherein R$^{11}$ and R$^{16}$ may be combined to form an alkylene group and to form a cyclo alkylene group having 5–10 carbon atoms with adjacent carbon atoms, and X shows a divalent group of —OC(R$^{17}$R$^{18}$)—C(R$^{19}$R$^{20}$) O—, wherein each of R$^{17}$ through R$^{20}$ individually represents a hydrogen atom, alkyl group, cycloalkyl group, or aryl group, provided that when R$^{14}$ is a hydrogen atom, R$^{11}$ and R$^{16}$ may be combined to form an alkylene group and to form a cyclo alkylene group having 5–10 carbon atoms with adjacent carbon atoms.

2. A method for manufacturing an allylphosphonate ester of claim 1 wherein the method comprises a step of:

reacting, in the presence of a palladium catalyst, a diene compound expressed by general formula (IV):

$$R^{11}R^{12}C=CR^{13}-CR^{14}=CR^{15}R^{16} \qquad (IV)$$

(in the formula (IV), each of $R^{11}$ through $R^{16}$ individually represents a hydrogen atom, alkyl group, cycloalkyl group, aryl group or aralkyl group, wherein, $R^{11}$ and $R^{16}$ may be combined to form an alkylene group or cyclo alkylene group);

with a secondary cyclic phosphonate ester expressed by general formula (V):

$$HP(O)X \qquad (V)$$

(in the formula (V), X shows a divalent group of $-OC(R^{17}R^{18})-C(R^{19}R^{20})O-$, wherein each of $R^{17}$ through $R^{20}$ individually represents a hydrogen atom, alkyl group, cycloalkyl group, or aryl group.

3. A method in accordance with claim 2 wherein the palladium catalyst is a zerovalent complex of palladium with a tertiary phosphine or tertiary phosphite as a ligand.

* * * * *